United States Patent [19]
Lenhart

[11] Patent Number: 6,001,090
[45] Date of Patent: Dec. 14, 1999

[54] THERMAL PHARMACEUTICAL DELIVERY SYSTEM

[76] Inventor: Douglas Lenhart, 4990 W. 60th Ter., Mission, Kans. 66205

[21] Appl. No.: 09/020,531

[22] Filed: Feb. 9, 1998

[51] Int. Cl.[6] ........................................................ A61K 9/22
[52] U.S. Cl. ........................... 604/890.1; 604/93; 604/114
[58] Field of Search ................................... 607/3; 604/93, 604/95, 20, 890.1, 48, 891.1, 113, 114

[56] References Cited

U.S. PATENT DOCUMENTS

| | | |
|---|---|---|
| 4,679,561 | 7/1987 | Doss . |
| 4,718,430 | 1/1988 | Holzer ..................................... 128/632 |
| 4,968,539 | 11/1990 | Aouagi et al. ............................... 428/1 |
| 4,989,601 | 2/1991 | Marchosky et al. ..................... 128/399 |
| 5,170,801 | 12/1992 | Casper et al. ............................ 128/769 |

OTHER PUBLICATIONS

James D. Doss and Charles McCabe; "Completely Implantable Hyperthermia Applicator With Externalized Temperature Monitoring: Tests in Conductive Gel[a)]"; Medical Physics, vol. 13(6), Nov./Dec. 1986, pp. 876–881.

James D. Doss and Charles W. McCabe; "Total Implants for Hyperthermia and Thermometry"; International Journal of Hyperthermia, vol. 4, No. 6, 1988, pp. 617–625.

*Primary Examiner*—Wynn Wood Coggins
*Assistant Examiner*—Deborah Blyveis
*Attorney, Agent, or Firm*—Hovey, Williams, Timmons & Collins

[57] ABSTRACT

A preferred thermal pharmaceutical delivery apparatus (10) includes a drug delivery unit (12) including a drug absorbent gel body (16) capable of desorbing a drug upon being heated, a heating element (18) positioned within the gel body (16), and a power receiving antenna (20) coupled with the heating element (18). The drug delivery unit (12) can be implanted subcutaneously in vivo. The apparatus (10) further includes a power unit (14) having a controller (26) coupled with a sending antenna (28) configured for inductively coupling transdermally with the receiving antenna (20) for delivering electrical power thereto in order to heat the element (18) and release the drug from the gel body (16).

10 Claims, 1 Drawing Sheet

THERMAL PHARMACEUTICAL DELIVERY SYSTEM

BACKGROUND OF THE INVENTION

1. Field of the Invention

The present invention relates to the field of medicine and, in particular, to the field of in vivo drug delivery systems. A preferred thermal pharmaceutical delivery system includes an implantable drug delivery unit including a drug absorbent gel body capable of desorbing a drug upon being heated, a heating element positioned within the gel, and a power receiving antenna coupled with the heating element.

2. Description of the Prior Art

In the field of medicine, pharmaceuticals may be delivered into a patient by injection into the blood stream or injection into a particular site. These known delivery techniques are sometimes ineffective or are of reduced effectiveness for some medical conditions such as certain types of cancerous tumors.

For example, some drugs are known to be very effective on specific types of cancer cells. However, delivery by injection into the blood stream may result in objectionable side effects because of the impact of the drugs on healthy tissues. In other cases, effectiveness is reduced because the drugs do not transfer readily between the blood stream and the site of the cancerous tissue.

Direct injection into a particular site may be effective in certain cases and impractical in others. For example, some sites may be inaccessible using injection techniques or may require injections so frequent as to be objectionable.

SUMMARY OF THE INVENTION

The present invention solves the prior art problems mentioned above and provides a distinct advance in the state of the art. In particular, the pharmaceutical delivery system hereof provides an effective alternative in some cases for delivering precise amounts of selected pharmaceuticals to a specific site in vivo.

The preferred pharmaceutical delivery apparatus includes a delivery body in the form of a gel, a pharmaceutical held by the body, and a heating assembly for heating the gel in order to release the pharmaceutical. The preferred heating assembly includes a grid of heating wire embedded within the gel body for thermal coupling therewith. The grid is electrically coupled with a power receiving antenna configured for inductive coupling in order to receive power for heating the grid. The gel body and heating assembly are implantable subcutaneously in vivo.

The preferred apparatus also includes a power unit having a controller and a sending antenna. The controller delivers high frequency A.C. current to the sending antenna which is selectively placed adjacent the subcutaneous receiving antenna for inductive coupling therewith and transdermal transfer of electrical power thereto.

DETAILED DESCRIPTION OF THE PREFERRED EMBODIMENT

Figure 1:
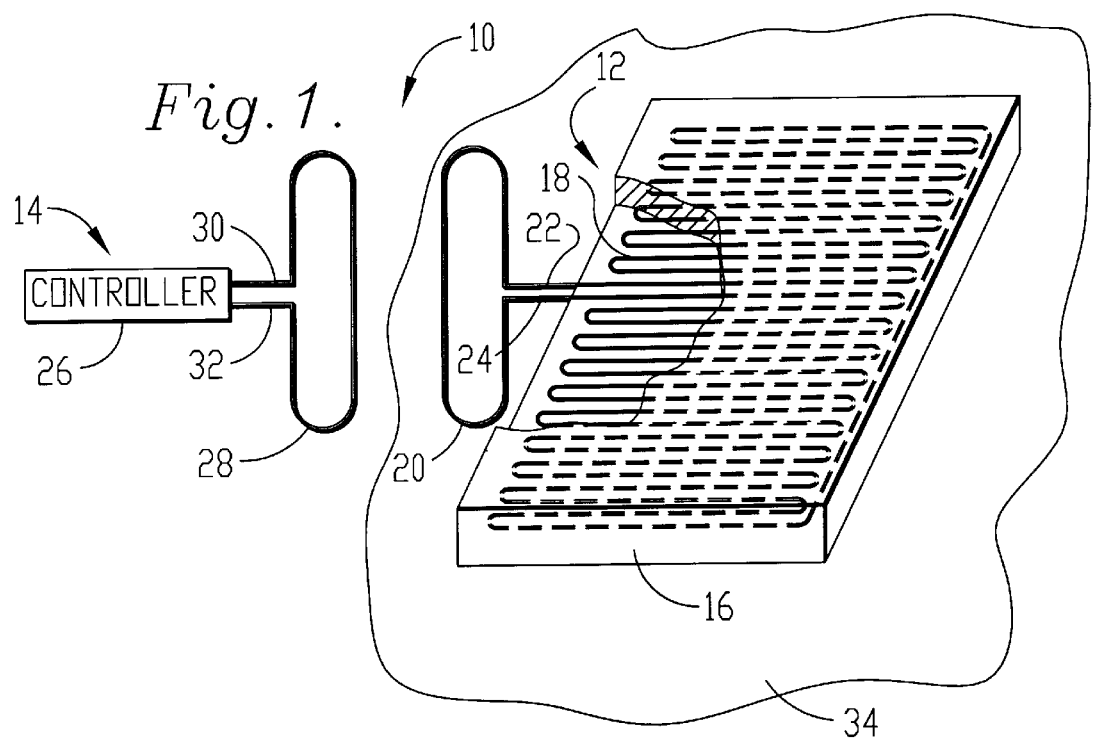
FIG. 1 is a schematic representation of the pharmaceutical delivery apparatus in accordance with the present invention shown with the delivery unit implanted subcutaneously in vivo.

FIG. 1 illustrates preferred pharmaceutical delivery apparatus 10 in accordance with the present invention. As used herein, the term "pharmaceutical" includes a medicinal drug. Apparatus 10 broadly includes drug delivery unit 12 and power unit 14.

Drug delivery unit 12 includes pharmaceutical delivery body 16, heating grid 18 and power receiving antenna 20 connected with grid 18 by lines 22 and 24. For use, body 16 includes a pharmaceutical held therein. Delivery unit 12 is configured for implantation subcutaneously in vivo.

Figure 2:
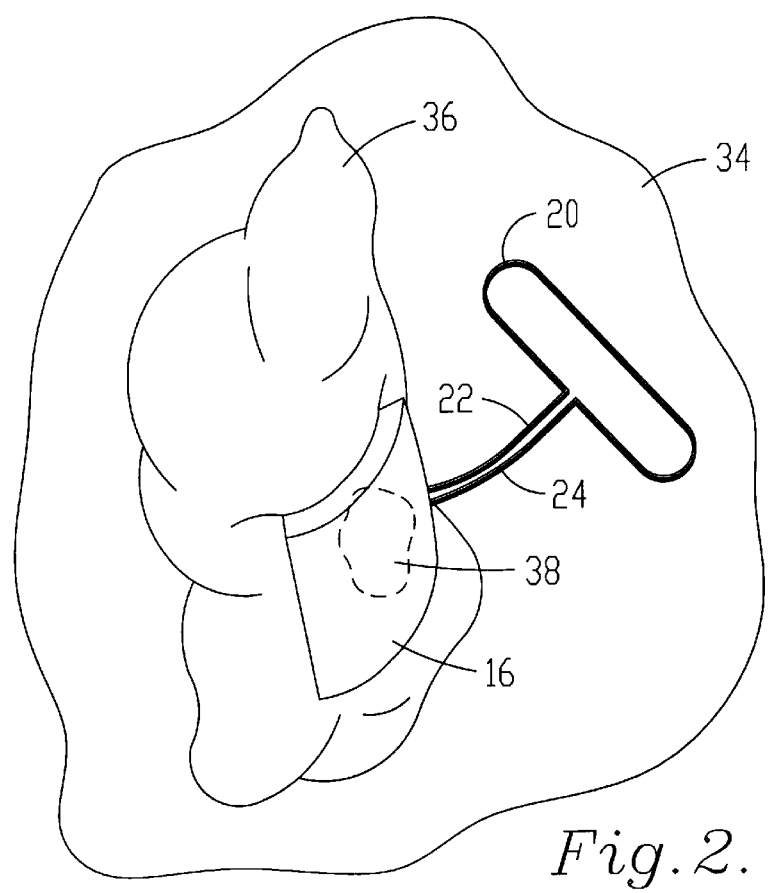
FIG. 2 is a view of the delivery unit of FIG. 1 shown with the gel body and embedded heating element formed about an organ at the site of a tumor.

Body 16 is composed of material suitable for implantation and capable of holding a pharmaceutical and releasing a pharmaceutical so held upon being heated. It is also preferred that the material be flexible and formretaining so that body 16 can be formed about a site such as illustrated in FIG. 2 and retains the form into which body 18 is shaped.

Suitable materials for body 16 include acrylimide gels, polyethylene gels and sylastic gels. Other examples include polypeptides and collagen. These materials are capable of absorbing pharmaceuticals and desorbing pharmaceuticals upon being heated. It will be appreciated that other types of materials may be suitable that hold pharmaceuticals in other ways such as adsorption and release the drug so held upon heating.

Heating grid 18 is preferably composed of a loop of heating wire embedded within body 16 so that grid 18 is thermally coupled therewith. It will be appreciated that other types of heating elements can be used so long as they are thermally coupled with body 16. For example, heating elements could be placed on the faces of body 16 or along the edges thereof.

In the preferred embodiment, the material forming body 16 is initially liquid and poured into a mold of the desired shape with grid 18 positioned therein. Grid 18 also serves as structural reinforcement for body 16 and assists in the flexibility and formretaining capability thereof.

Power receiving antenna 20 is configured for receiving electrical power from a source thereof through inductive coupling. Such types of antennas are known to those of ordinary skill in the art such as those used for implanted pacemakers and the like and for hyperthermic cancer therapy as illustrated in U.S. Pat. No. 4,679,561, the disclosure of which is hereby incorporated by reference. Lines 22,24 connect antenna 20 with grid 18 for providing electrical power thereto in order to heat grid 18 and thereby body 16.

Power unit 14 includes power controller 26 and power sending antenna 28 interconnected by lines 30 and 32. In the preferred embodiment, power unit 14 is the type described in U.S. Pat. No. 4,679,561 referenced above. Specifically, controller 26 is operable to produce a high frequency (e.g., 13.8 MHZ or in the microwave range above 1.0 GHz), power-controlled output. With sending antenna 28 adjacent receiving antenna 20 and inductively coupled therewith, power is delivered with very little loss. As a result, such can be accomplished transdermally. Moreover, controller 26 allows selective control of the amplitude and timing of the output enabling selective control of the power output and thereby selective control over the heating of body 16. In turn, this leads to precise control over the amount and timing of pharmaceutical release from body 16.

In the method of the present invention of delivering a pharmaceutical to a patient, drug delivery unit 12 is implanted subcutaneously in vivo in patient 34 as illustrated. Referring to FIG. 2, the flexible nature of body 16 allows it to be formed about a specific site such as organ 36 having tumor 38. This also assists in retaining delivery body 16 at the site. Delivery body 16 includes the selected pharmaceutical or pharmaceuticals absorbed therein. Such can include anti-angeogenesis and anti-neoplastic drugs, for example, which are most effective when delivered closely to the site such as tumor 38. Other specific examples include the drugs known as F5U for treating urinary tract cancers and cysplatinum for treating prostate cancer.

Power receiving antenna 20 is positioned at a convenient location such as just below the skin of the abdomen. Lines 22 and 24 are routed as needed for the interconnection between grid 18 and antenna 20.

In order to release the pharmaceutical from body 16, power sending antenna 28 is placed against the skin adjacent receiving antenna 20 positioned so that these antennas can couple inductively. Power controller 26 is then operated to provide power as prescribed for the delivery of the pharmaceuticals. That is, sending antenna 28 delivers the power as received from controller 26 to receiving antenna 20 transdermally. The power received by antenna 20 then delivered over lines 22 and 24 to heating grid 18 which in turn heats body 16. In response, body 16 desorbs the pharmaceutical in relation to the amount of heat applied by grid 18.

Apparatus 10 enables very precise control of pharmaceutical application both in terms of dosage and time. For example, controller 26 can be operated to deliver a small precise dosage of the pharmaceutical over a relatively long time frame. This type of application is often desirable for very powerful anti-cancer drugs. In other applications, a so-called pulse dosage scheme may be most effective. In this scheme a relatively large amount of pharmaceutical is delivered over a relatively short time frame. The present invention enables the delivery of the pharmaceutical as desired for the greatest effectiveness.

As those skilled in the art will appreciate, the present invention encompasses many variations in the preferred embodiment described herein. For example, body 16 can be molded into any shape as needed for effective treatment. Different types of heating elements can be used for heating delivery body. Also, other types of configurations can be used for delivering power to the grid such as bringing the connection lines through the skin for external connection. As a final example, there are a wide variety of designs available for providing power to the heating grid other than the preferred controller. Having thus described the preferred embodiment of the present invention, the following is claimed as new and desired to be secured by Letters Patent:

What is claim is:

1. A pharmaceutical delivery apparatus comprising:
    a pharmaceutical delivery body composed of a semisolid material capable of holding a pharmaceutical and releasing a pharmaceutical upon being heated; and
    electrical heating means thermally coupled with said body for receiving electrical power from a source thereof and for selectively electrically heating said body for selectively releasing a pharmaceutical held therein.

2. A pharmaceutical delivery apparatus comprising:
    a pharmaceutical delivery body composed of material capable of holding a pharmaceutical and releasing a pharmaceutical upon being heated, and
    electrical heating means thermally coupled with said body for receiving electrical power from a source thereof and for selectively electrically heating said body for selectively releasing a pharmaceutical held therein,
    said body being composed of material selected from the group consisting of acrylimide gels, polyethylene gels, sylastic gels, polypeptides and collagen.

3. The apparatus as set forth in claim 1, said body being flexible and form-retaining.

4. The apparatus as set forth in claim 1, said heating means including a heating element thermally coupled with said body.

5. The apparatus as set forth in claim 4, said heating element including a grid of electrical heating wire embedded within said body.

6. The apparatus as set forth in claim 1, said heating means including a heating element thermally coupled with said body and a power receiving antenna electrically coupled with said heating element and configured for receiving electrical power from a source thereof by way of inductive coupling and for delivering power so received to said heating element for heating said element and thereby said body.

7. A pharmaceutical delivery apparatus comprising:
    a pharmaceutical delivery body composed of material capable of holding a pharmaceutical and releasing a pharmaceutical upon being heated; and
    electrical heating means thermally coupled with said body for receiving electrical power from a source thereof and for selectively electrically heating said body for selectively releasing a pharmaceutical held therein,
    said heating means including a heating element thermally coupled with said body and a power receiving antenna electrically coupled with said heating element and configured for receiving electrical power from a source thereof by way of inductive coupling and for delivering power so received to said heating element for heating said element and thereby said body,
    said heating element including heating wire formed into a grid and embedded within said body.

8. A pharmaceutical delivery apparatus comprising:
    a pharmaceutical delivery body composed of material capable of holding a pharmaceutical and releasing a pharmaceutical upon being heated;
    electrical heating means thermally coupled with said body for receiving electrical power from a source thereof and for selectively electrically heating said body for selectively releasing a pharmaceutical held therein,
    said heating means including a heating element thermally coupled with said body and a power receiving antenna electrically coupled with said heating element and configured for receiving electrical power from a source thereof by way of inductive coupling and for delivering power so received to said heating element for heating said element and thereby said body; and
    a power unit including a power controller coupled with a power sending antenna configured for inductively coupling with said receiving antenna for delivering electrical power thereto.

9. The apparatus as set forth in claim 8, said body, pharmaceutical and heating means being implantable subcutaneously in vivo, said antennas being configured for inductively coupling transdermally.

10. A pharmaceutical delivery apparatus comprising:
    a pharmaceutical delivery body composed of material capable of holding a pharmaceutical and releasing a pharmaceutical upon being heated; and
    electrical heating means thermally coupled with said body for receiving electrical power from a source thereof and for selectively electrically heating said body for selectively releasing a pharmaceutical held therein,
    said delivery body including a pharmaceutical held therein and being flexible, form-retaining, and composed of material selected from the group consisting of acrylimide gels, polyethylene gels, sylastic gels, polypeptides and collagen, said heating means including heating wire formed into a grid and embedded within said delivery body and thermally coupled therewith, and including a receiving antenna electrically coupled with said heating element and configured for receiving electrical power from a source thereof by way of inductive coupling and for delivering power so received to said heating element for heating said element and thereby said body, said apparatus further including a power unit including a controller coupled with a sending antenna configured for inductively coupling with said receiving antenna for delivering electrical power thereto, said body, pharmaceutical and heating means being implantable subcutaneously in vivo, said antennas being configured for inductively coupling transdermally.

* * * * *